United States Patent
Zhang et al.

(10) Patent No.: US 7,930,022 B2
(45) Date of Patent: Apr. 19, 2011

(54) SYSTEM AND METHOD TO DETERMINE HEMODYNAMIC TOLERABILITY

(75) Inventors: Yi Zhang, Blaine, MN (US); Allan C. Shuros, St. Paul, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 300 days.

(21) Appl. No.: 11/745,016

(22) Filed: May 7, 2007

(65) Prior Publication Data

US 2008/0281367 A1 Nov. 13, 2008

(51) Int. Cl.
*A61N 1/362* (2006.01)
(52) U.S. Cl. .......................................... 607/4
(58) Field of Classification Search ................ 607/4
See application file for complete search history.

(56) References Cited

U.S. PATENT DOCUMENTS

| | | | |
|---|---|---|---|
| 4,830,006 | A | 5/1989 | Haluska et al. |
| 5,163,429 | A | 11/1992 | Cohen |
| 5,183,040 | A | 2/1993 | Nappholz et al. |
| 5,282,840 | A | 2/1994 | Hudrlik |
| 5,311,874 | A | 5/1994 | Baumann et al. |
| 5,330,505 | A | 7/1994 | Cohen |
| 5,788,717 | A | 8/1998 | Mann et al. |
| 5,797,395 | A | 8/1998 | Martin |
| 5,897,575 | A | 4/1999 | Wickham |
| 5,978,707 | A | 11/1999 | Krig et al. |
| 5,999,854 | A | 12/1999 | Deno et al. |
| 6,044,298 | A | 3/2000 | Salo et al. |
| 6,101,414 | A | 8/2000 | Kroll |
| 6,217,525 | B1 * | 4/2001 | Medema et al. ............... 600/508 |
| 6,278,894 | B1 | 8/2001 | Salo et al. |
| 6,314,323 | B1 | 11/2001 | Ekwall et al. |
| 6,493,579 | B1 | 12/2002 | Gilkerson et al. |
| 6,522,914 | B1 | 2/2003 | Huvelle |
| 6,522,925 | B1 | 2/2003 | Gilkerson et al. |
| 6,654,639 | B1 | 11/2003 | Lu |
| 6,708,058 | B2 | 3/2004 | Kim et al. |

(Continued)

FOREIGN PATENT DOCUMENTS

EP 0310026 A2 4/1989

(Continued)

OTHER PUBLICATIONS

Khoury et al. Continuous Right Ventricular Volume Assessment by Catheter Measurement of Impedance for Antitachycardia System Control. Pacing Clin. Electrophysiol. 12(12):(Dec. 1989), 1918-1926.*

(Continued)

*Primary Examiner* — Carl H Layno
*Assistant Examiner* — Jeremiah T Kimball
(74) *Attorney, Agent, or Firm* — Schwegman, Lundberg & Woessner, P.A.

(57) ABSTRACT

An implantable medical device detects a tachyarrhythmia of a heart. During the detected tachyarrhythmia, the device determines a local myocardial impedance. Using the local myocardial impedance, the device determines whether there is sufficient perfusion to the heart. The device can then either deliver a less aggressive device therapy in response to the detected tachyarrhythmia when there is sufficient perfusion to the heart, or deliver a more aggressive device therapy in response to the detected tachyarrhythmia when there is insufficient perfusion to the heart. The perfusion information can also be used to alter tachyarrhythmia detection or classification.

30 Claims, 8 Drawing Sheets

U.S. PATENT DOCUMENTS

| | | | |
|---|---|---|---|
| 6,775,572 B2 | 8/2004 | Zhu et al. | |
| 6,873,870 B2 | 3/2005 | Ferek-Petric | |
| 6,885,890 B2 | 4/2005 | Spinelli et al. | |
| 6,988,995 B2* | 1/2006 | Zhou et al. | 600/558 |
| 7,010,344 B2 | 3/2006 | Burnes et al. | |
| 7,010,347 B2* | 3/2006 | Schecter | 607/17 |
| 7,130,681 B2 | 10/2006 | Gebhardt et al. | |
| 7,228,173 B2 | 6/2007 | Cazares | |
| 7,239,915 B2 | 7/2007 | Cohen | |
| 7,277,750 B2 | 10/2007 | Perschbacher et al. | |
| 7,283,871 B1* | 10/2007 | Hofstadter et al. | 607/5 |
| 7,349,740 B2 | 3/2008 | Soykan et al. | |
| 2003/0083703 A1 | 5/2003 | Zhu et al. | |
| 2003/0204209 A1* | 10/2003 | Burnes et al. | 607/14 |
| 2003/0208240 A1 | 11/2003 | Pastore et al. | |
| 2004/0215097 A1 | 10/2004 | Wang | |
| 2004/0220634 A1 | 11/2004 | Belk | |
| 2004/0220636 A1 | 11/2004 | Burnes | |
| 2004/0230129 A1 | 11/2004 | Haefner | |
| 2005/0049646 A1 | 3/2005 | Czygan et al. | |
| 2005/0149135 A1 | 7/2005 | Krig et al. | |
| 2005/0222629 A1 | 10/2005 | Perschbacher et al. | |
| 2006/0089675 A1 | 4/2006 | Burnes et al. | |
| 2006/0122651 A1 | 6/2006 | Whitman | |
| 2006/0184060 A1 | 8/2006 | Belalcazar et al. | |
| 2006/0235326 A1 | 10/2006 | Dzwonczyk et al. | |
| 2007/0043394 A1 | 2/2007 | Zhang et al. | |
| 2007/0135848 A1 | 6/2007 | Kim et al. | |
| 2007/0142866 A1 | 6/2007 | Li | |
| 2007/0149890 A1 | 6/2007 | Li et al. | |
| 2007/0173894 A1 | 7/2007 | Li | |
| 2007/0197928 A1 | 8/2007 | Kim et al. | |
| 2007/0203524 A1* | 8/2007 | Sheldon et al. | 607/9 |
| 2009/0318985 A1 | 12/2009 | Shuros et al. | |

FOREIGN PATENT DOCUMENTS

| | | | |
|---|---|---|---|
| EP | 1384433 A1 | | 1/2004 |
| EP | 1582233 A2 | | 10/2005 |
| WO | WO-9519806 A1 | | 7/1995 |
| WO | WO-95/20348 A1 | | 8/1995 |
| WO | WO-03090858 A1 | | 11/2003 |
| WO | WO 2004098389 A2 | * | 11/2004 |
| WO | WO-2006/041337 A1 | | 4/2006 |
| WO | WO-2006088805 A2 | | 8/2006 |
| WO | WO-2007078421 A2 | | 7/2007 |
| WO | WO-2007078421 A3 | | 7/2007 |
| WO | WO-2008/137166 A1 | | 11/2008 |

OTHER PUBLICATIONS

Salazar et al. Transmural Versus Nontransmural In Situ Electrical Impedance Spectrum for Healthy, Ischemic, and Healed Myocardium. Biomed. Eng. vol. 51, No. 8 (2004), 1421-1427.*

Lee et al. Decision Boundary Feature Extraction for Nonparametric Classification. IEEE Transactions on Systems, Man, and Cybernetics. (1993) vol. 23, No. 2. 433-444.*

Fallert, Michael A., et al., "Myocardial Electrical Impedance Mapping of Ischemic Sheep Hearts and Healing Aneurysms", *Circulation* 87(1), (Jan. 1993), 199-207.

Kaye, Gerry, et al., "Can transventricular intracardiac impedance measurement discriminate haemodynamically unstable ventricular arrhythmias in human?", *Europace*, vol. 9, (2007), 122-126.

Kaye, Gerry, et al., "The use of unipolar intracardiac impedance for discrimination of haemodynamically stable and unstable arrythmias in man", *Europace*, vol. 8, (2006), 988-993.

Khoury, Dirar, et al., "Continuous right ventricular volume assessment by catheter measurement of impedance for antitachycardia system control.", *Pacing Clin Electrophysiol.*, 12(12), (Dec. 1989), 1918-1926.

Salazar, Y., et al., "Transmural versus nontransmural in situ electrical impedance spectrum for healthy, ischemic and healed myocardium", *Biomed. Eng.*, vol. 51, No. 8, (2004), 1421-1427.

Wood, M. A., et al., "Comparison of right ventricular impedance, pulse pressure and maximal dP/dt for determination of hemodynamic stability of ventricular arrhythmias associated with coronary artery disease", *Am J Cardiol.*, 66(5), (Sep. 1, 1990), 575-82.

"Application Serial No. PCT/US2008/005832, International Search Report mailed Sep. 18, 2008", 5 pgs.

"Application Serial No. PCT/US2008/005832, Written Opinion mailed Sep. 18, 2008", 9 pgs.

"Application Serial No. PCT/US2008/005832, Written Opinion of the International Searching Authority", 9 pgs.

Steinbach, K. K, et al., "Hemodynamics during ventricular tachyarrhythmias", *American Heart Journal*, 127(4, Part 2), (Apr. 1994), 1102-1106.

* cited by examiner

SYSTEM AND METHOD TO DETERMINE HEMODYNAMIC TOLERABILITY

TECHNICAL FIELD

This document pertains generally to implantable medical devices, and more particularly, but not by way of limitation, to implantable medical devices configured to determine hemodynamic tolerability.

BACKGROUND

Hemodynamics relate to the adequate supply of blood throughout a body via the workings of the heart. Perfusion refers to the adequate supply of blood to, into, or through a particular organ or tissue of the body. Insufficient perfusion to one or more organs or tissues in the body normally results in inadequate hemodynamics. In the case of perfusion to the heart, a lack of blood supply to the heart results in ischemia. Ischemia can cause an overall diminished heart function, and normally should be treated in some manner by a physician.

OVERVIEW

This overview is intended to provide an overview of the subject matter of the present patent application. It is not intended to provide an exclusive or exhaustive explanation of the invention. The detailed description is included to provide further information about the subject matter of the present patent application.

In Example 1, a process of using an implantable medical device includes detecting a tachyarrhythmia of a heart using the implantable medical device, delivering a non-stimulatory electrical energy to the heart during the detected tachyarrhythmia using the implantable medical device, determining a myocardial impedance by measuring a response to the non-stimulatory electrical energy, determining, during the detected tachyarrhythmia and using the myocardial impedance, whether there is sufficient perfusion to the heart; delivering a less aggressive device therapy in response to the detected tachyarrhythmia when the myocardial impedance indicates that there is sufficient perfusion to the heart, and delivering a more aggressive device therapy in response to the detected tachyarrhythmia when the myocardial impedance indicates that there is insufficient perfusion to the heart.

In Example 2, the less aggressive therapy of Example 1 optionally includes Anti-Tachyarrhythmia Pacing (ATP) and the more aggressive therapy includes a shock.

In Example 3, the determination of whether there is sufficient perfusion to the heart of Examples 1-2 optionally includes identifying a change in myocardial impedance at a particular frequency of the non-stimulatory electrical energy.

In Example 4, the identification of a change in myocardial impedance of Examples 1-3 optionally includes comparing the myocardial impedance to a baseline myocardial impedance or comparing the myocardial impedance to an absolute threshold.

In Example 5, the particular frequency of the non-stimulatory electrical energy of Examples 1-4 optionally includes a frequency value that is in an inclusive range of approximately 5-30 kHz.

In Example 6, the determination of whether there is sufficient perfusion to the heart of Examples 1-5 optionally includes identifying an increase in myocardial impedance frequency response magnitude over a plurality of frequencies at which the non-stimulatory electrical energy is delivered to the heart.

In Example 7, the plurality of frequencies of Examples 1-6 optionally includes different frequencies within an inclusive range of between 1 kHz and 100 kHz.

In Example 8, the determination of whether there is sufficient perfusion to the heart of Examples 1-7 optionally includes identifying a change in myocardial impedance magnitude frequency dependence over a plurality of frequencies at which the non-stimulatory electrical energy is delivered to the heart.

In Example 9, the plurality of frequencies of Examples 1-8 optionally includes different frequencies within an inclusive range of between 1 kHz and 100 kHz.

In Example 10, the determination of whether there is sufficient perfusion to the heart of Examples 1-9 optionally includes identifying a change in myocardial impedance frequency response phase over a plurality of frequencies at which the non-stimulatory electrical energy is delivered to the heart.

In Example 11, the plurality of frequencies of Examples 1-10 optionally includes different frequencies within an inclusive range of between 5 kHz and 30 kHz.

In Example 12, the delivery of the non-stimulatory electrical energy of Examples 1-11 optionally includes delivering a current defining a current vector, and the measurement of a response to the delivered non-stimulatory electrical energy of Examples 1-11 optionally includes measuring a response voltage defining a substantially orthogonal voltage vector.

In Example 13, the processes of Examples 1-12 optionally include combining data relating to the detected tachyarrhythmia and data relating to the perfusion, and using the combined data to determine whether to deliver a less aggressive therapy or a more aggressive therapy to the heart.

In Example 14, the combined data of Examples 1-13 optionally includes a plot of electrocardiogram data versus impedance data, and the process of Examples 1-13 optionally include calculating an optimal decision hyperplane or a discrete classification zone in a feature space.

In Example 15, the processes of Examples 1-14 optionally include altering a tachyarrhythmia detection algorithm or a tachyarrhythmia classification technique as a function of the perfusion to the heart.

In Example 16, an implantable medical device includes a control circuit, a tachyarrhythmia detection circuit coupled to the control circuit, an electrical energy delivery circuit, coupled to the control circuit, the electrical delivery circuit configured to deliver non-stimulatory electrical energy to a heart during a detected tachyarrhythmia, an impedance detection circuit, coupled to the control circuit, the impedance detection circuit configured to detect a myocardial impedance by measuring a response to the non-stimulatory electrical energy, a perfusion measurement circuit, coupled to the control circuit, the perfusion measurement circuit configured to determine, during a detected tachyarrhythmia and using the myocardial impedance, whether there is sufficient perfusion to the heart, a therapy delivery circuit, the therapy delivery circuit configured to deliver a less aggressive therapy in response to the detected tachyarrhythmia when the myocardial impedance indicates that there is sufficient perfusion to the heart and to deliver a more aggressive therapy in response to the detected tachyarrhythmia when the myocardial impedance indicates that there is insufficient perfusion to the heart.

In Example 17, the therapy delivery circuit of Example 16 is optionally configured to deliver Anti-Tachyarrhythmia Pacing (ATP) as the less aggressive therapy and shock as the more aggressive therapy.

In Example 18, the perfusion measurement circuit of Examples 16-17 is optionally configured to determine whether there is sufficient perfusion to the heart by identifying a change in myocardial impedance magnitude at a particular frequency of the non-stimulatory electrical energy.

In Example 19, the perfusion measurement circuit of Examples 16-18 is optionally configured to identify the change in myocardial impedance magnitude by comparing the myocardial impedance magnitude to a baseline myocardial impedance magnitude or comparing the myocardial impedance magnitude to an absolute threshold value.

In Example 20, the electrical energy delivery circuit of Examples 16-19 is optionally configured to deliver the particular frequency of the non-stimulatory electrical energy in an inclusive range of approximately 5-30 kHz.

In Example 21, the perfusion measurement circuit of Examples 16-20 is optionally configured to determine whether there is sufficient perfusion to the heart by identifying an increase in myocardial impedance frequency response magnitude over a plurality of frequencies at which the non-stimulatory electrical energy is delivered to the heart.

In Example 22, the electrical energy delivery circuit of Examples 16-21 optionally delivers the plurality of frequencies within an inclusive range of between 1 kHz and 100 kHz.

In Example 23, the perfusion measurement circuit of Examples 16-22 is optionally configured to determine whether there is sufficient perfusion to the heart by identifying a change in myocardial impedance frequency dependence over a plurality of frequencies at which the non-stimulatory electrical energy is delivered to the heart.

In Example 24, the electrical energy deliver circuit of Examples 16-23 optionally delivers the plurality of frequencies within an inclusive range of between 1 kHz and 100 kHz.

In Example 25, the perfusion measurement circuit of Examples 16-24 is optionally configured to determine whether there is sufficient perfusion to the heart by identifying a change in myocardial impedance frequency response phase over a plurality of frequencies at which the non-stimulatory electrical energy is delivered to the heart.

In Example 26, the electrical energy delivery circuit of Examples 16-25 optionally delivers the plurality of frequencies within an inclusive range of between 5 kHz and 30 kHz.

In Example 27, the electrical delivery circuit of Examples 16-26 is optionally configured to deliver the non-stimulatory electrical energy by delivering a current defining a current vector, and wherein measuring a response to the delivered non-stimulatory electrical energy of Examples 16-26 optionally includes measuring a response voltage defining a substantially orthogonal voltage vector.

In Example 28, the tachyarrhythmia detection circuit of Examples 16-27 is optionally configured to use the perfusion to the heart for altering a technique for the detecting or classifying the tachyarrhythmia.

In Example 29, an implantable medical device includes a means for detecting a tachyarrhythmia of a heart using the implantable medical device, a means for delivering a non-stimulatory electrical energy to the heart during the detected tachyarrhythmia using the implantable medical device, a means for determining a myocardial impedance by measuring a response to the non-stimulatory electrical energy, a means for determining, during the detected tachyarrhythmia and using the myocardial impedance, whether there is sufficient perfusion to the heart, a means for delivering a less aggressive device therapy in response to the detected tachyarrhythmia when the myocardial impedance indicates that there is sufficient perfusion to the heart, and a means for delivering a more aggressive device therapy in response to the detected tachyarrhythmia when the myocardial impedance indicates that there is insufficient perfusion to the heart.

BRIEF DESCRIPTION OF THE DRAWINGS

In the drawings, which are not necessarily drawn to scale, like numerals may describe substantially similar components in different views. Like numerals having different letter suffixes may represent different instances of substantially similar components. The drawings illustrate generally, by way of example, but not by way of limitation, various examples discussed in the present document.

DETAILED DESCRIPTION

The following detailed description includes references to the accompanying drawings, which form a part of the detailed description. The drawings show, by way of illustration, specific embodiments in which the invention may be practiced. These embodiments are also referred to herein as "examples." The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one, independent of any other usages of "at least one" or "one or more." In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
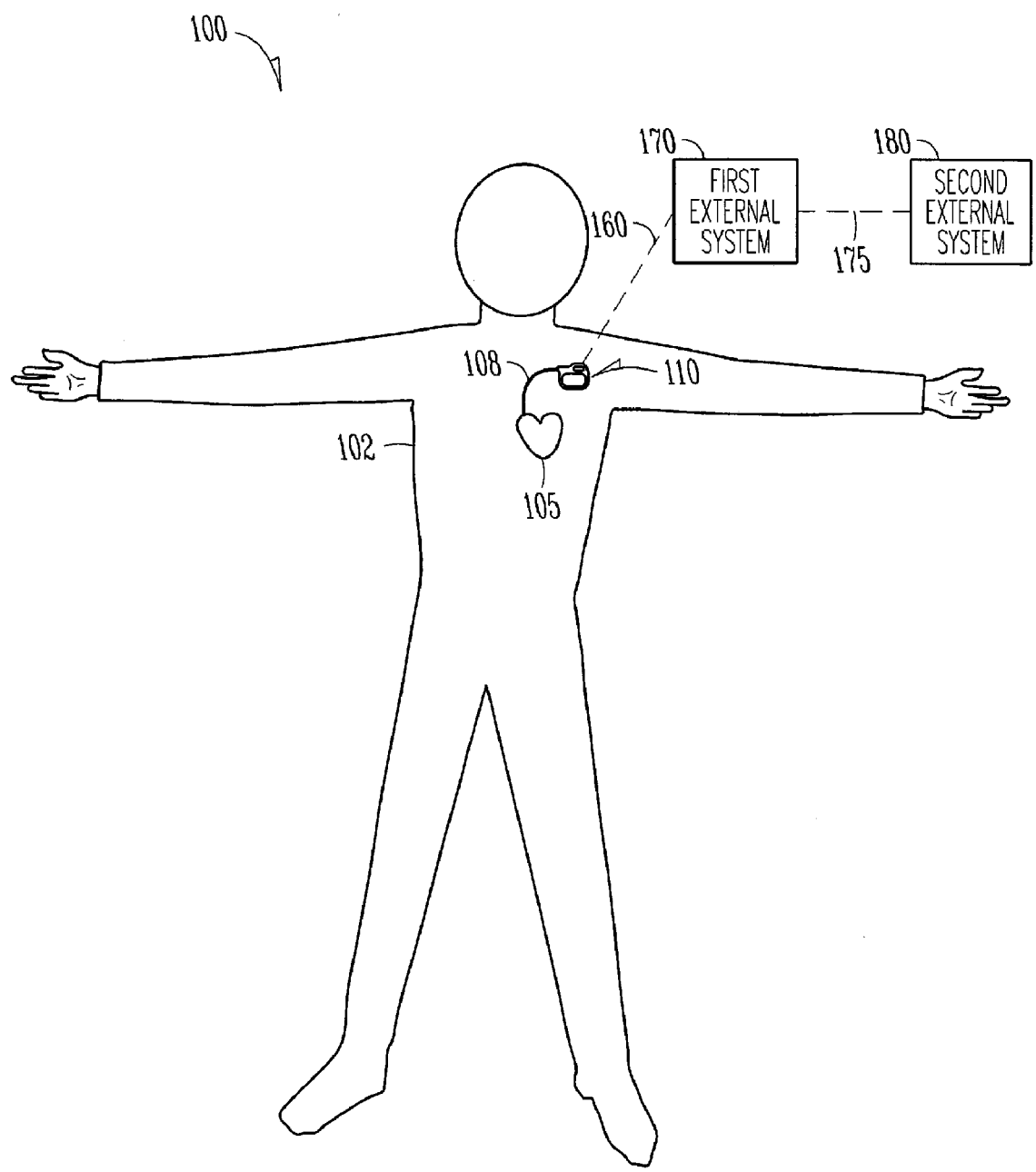
FIG. 1 illustrates an example of an implanted medical device in communication with external devices via a telemetry system.

FIG. 1 is a diagram illustrating an example of a medical device system 100, and portions of an environment in which it is used. The environment includes a body 102 with a heart 105. The system 100 includes an implantable medical device 110, a lead system 108, a first adjunct device or external system 170, a second adjunct device or external system 180, and a wireless telemetry link 160. The system 100 can be a leadless system that does not have the lead system 108. The first external system 170 can be coupled to the second external system 180 via a wired or wireless communications link 175. The first external system 170 can be referred to as a local external system, and the second external system 180 can be referred to as a remote external system. Heart rate data, therapy delivery data (such as pacing data or drug titration data), electrogram data, hemodynamic data, perfusion data, or other data can be transferred from the device 110 to the external system 170 via the telemetry link 160. The telemetered data loaded into the external system 170 can then be used for analysis and interpretation either immediately or at a later time.

Figure 2:
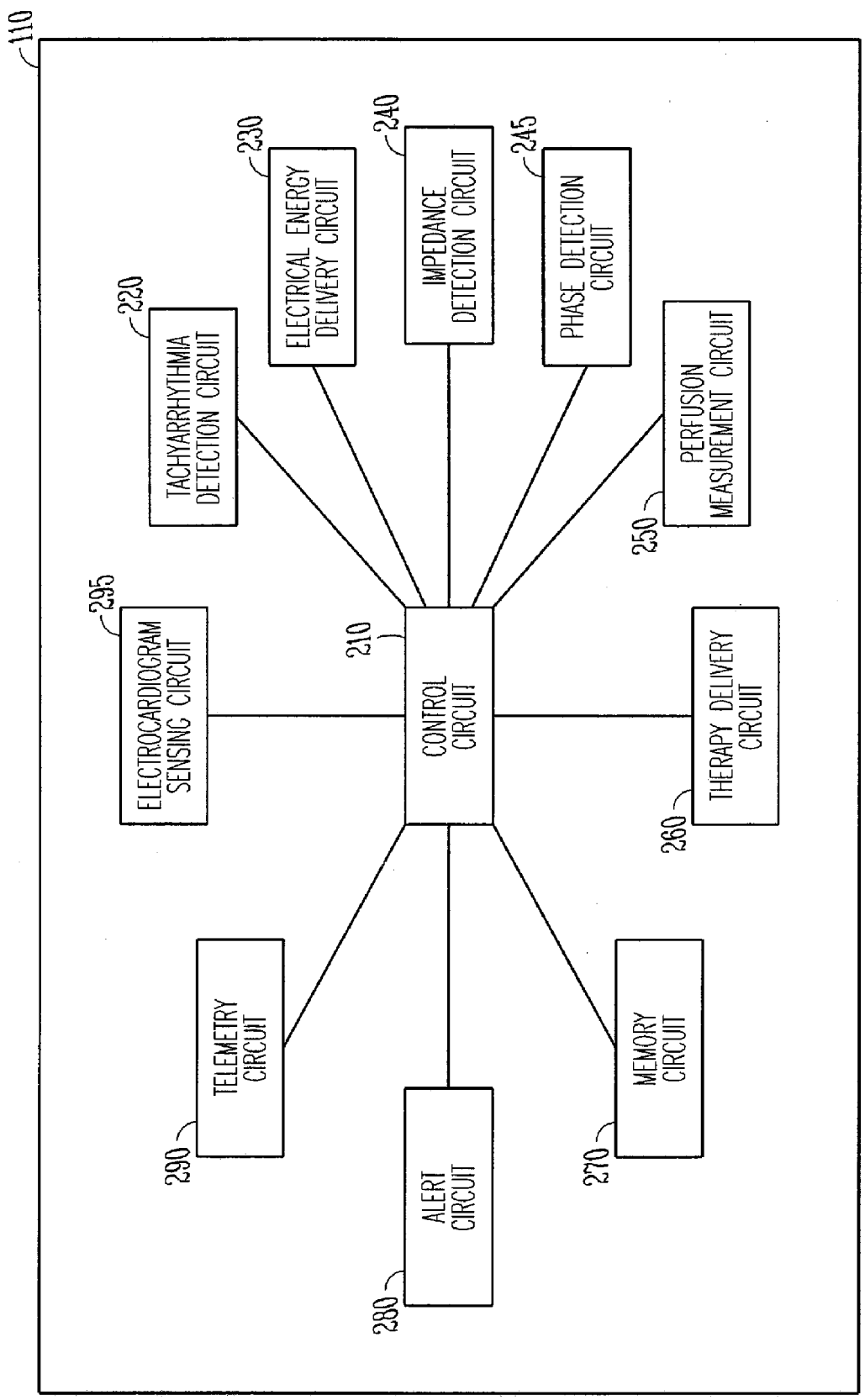
FIG. 2 illustrates an example of a block diagram of an implantable medical device.

FIG. 2 illustrates an example of the implantable medical device 110 of FIG. 1. In this example, the device 110 includes a control circuit 210. A tachyarrhythmia detection circuit 220 can be coupled to the control circuit 210. An electrical energy delivery circuit 230 can be coupled to the control circuit 210. The electrical energy delivery circuit 230 can be configured to deliver non-stimulatory electrical energy to a heart such as during a detected tachyarrhythmia. An impedance detection circuit 240 can be coupled to the control circuit 210. The impedance detection circuit 240 can be configured to detect an indication of a myocardial impedance such as by measuring a response to the non-stimulatory electrical energy delivered by the electrical energy delivery circuit 230. In an example, the impedance detection circuit 240 can be configured to detect a localized myocardial impedance. In an illustrative example, a non-stimulatory current is delivered and a responsive voltage is measured to provide the indication of impedance. A phase detection circuit 245 can be coupled to the control circuit 210. The phase detection circuit 245 can be configured to detect a phase shift in response to the non-stimulatory electrical energy delivered by the electrical delivery circuit 230. A perfusion measurement circuit 250 can be coupled to the control circuit 210. The perfusion measurement circuit 250 can be configured to determine, such as during a detected tachyarrhythmia and using the myocardial impedance magnitude or its phase shift, whether there is sufficient perfusion to the heart. A therapy delivery circuit 260 can be coupled to the control circuit 210. The therapy delivery circuit 260 can be configured to deliver a less aggressive therapy to a heart in response to the detected tachyarrhythmia when the myocardial impedance or phase shift indicates that there is sufficient perfusion to the heart. In an example, such less aggressive therapy can be Anti-Tachyarrhythmia Pacing (ATP). The therapy delivery circuit 260 can be further configured to deliver a more aggressive therapy in response to the detected tachyarrhythmia when the myocardial impedance or phase shift indicates that there is insufficient perfusion to the heart. In an example, a more aggressive therapy can be a shock therapy. In another example, the therapy delivery circuit can include a drug titration circuit. For example, if the perfusion measurement circuit 250 senses insufficient perfusion to the heart, an appropriate drug may be titrated into the patient to treat the condition. The implantable medical device 110 can further include a memory circuit 270, an alert circuit 280, a telemetry circuit 290, and a electrocardiogram sensing circuit 295, all of which can be coupled to the control circuit 210.

In an example, the implantable medical device 110 can be a cardiac rhythm management device. In an example, the telemetry circuit 290 can be configured to communicate with the external system 170. The external system 170 can include a local external system. The local external system can be attachable to a patient's body, or it can be a system that is separate from a patient's body. The external device can also include a remote external device 180, such as a device to which a patient's physician can have access. In a system with a remote external device 180, a local external device 170 can be configured to communicate with the remote external device 180.

Figure 3:
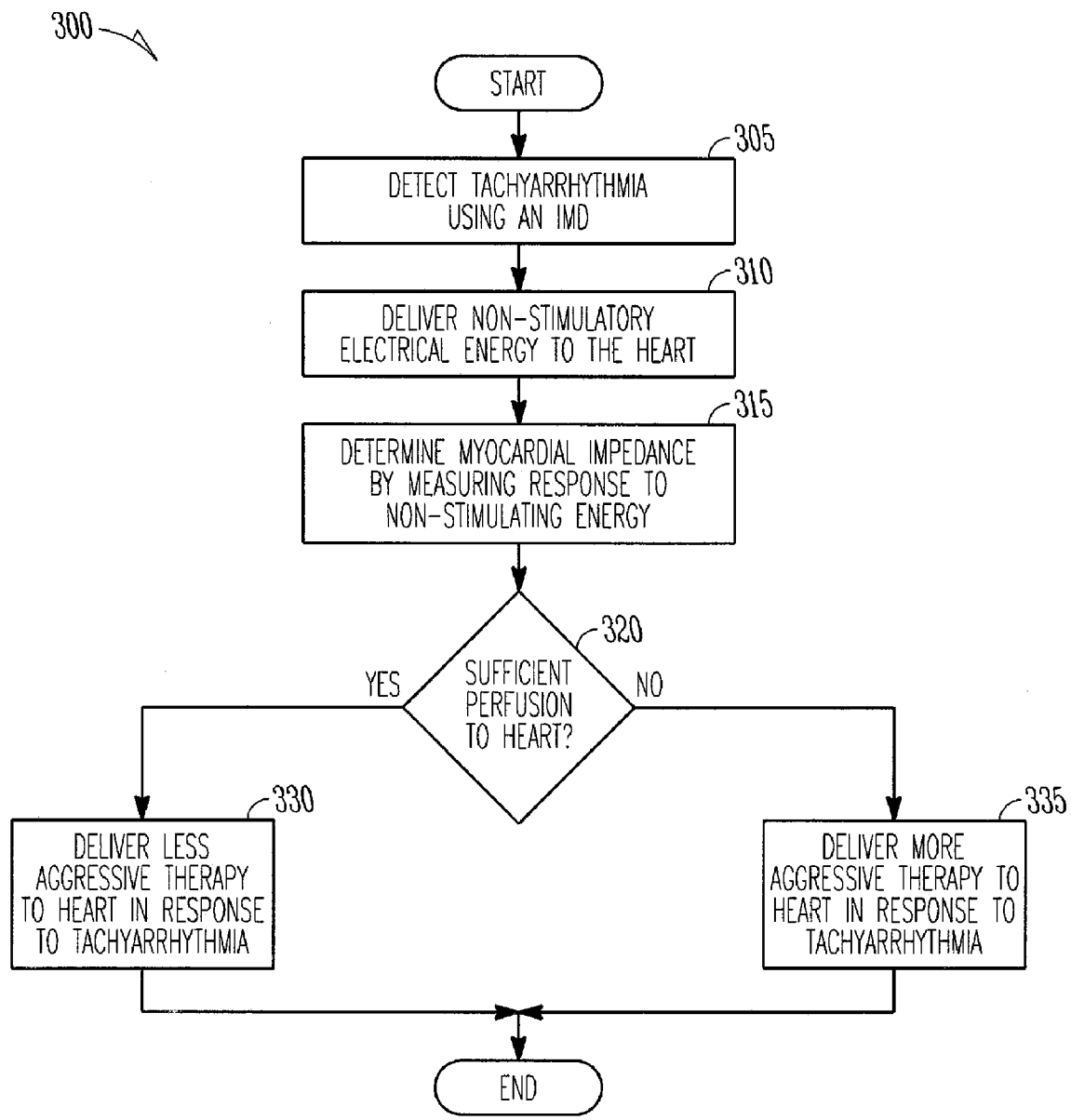
FIG. 3 illustrates an example process to provide electrical stimulation therapy to a patient as a function of perfusion to the patient's heart.

FIG. 3 illustrates an example of a process 300 to determine the hemodynamic stability of a patient using an implantable medical device such as the implantable medical device 110 of FIG. 2. The operations illustrated in FIG. 3 need not all be executed, the operations need not be executed in the order as illustrated in FIG. 3, and systems other than the implantable medical device 110 of FIG. 2 can be used to implement all or part of the process 300 of FIG. 3.

In process 300, at 305, a tachyarrhythmia of a heart, such as a ventricular tachyarrhythmia or a super ventricular tachyarrhythmia, is detected using an implantable medical device. For example, an electrocardiogram can be sensed by a circuit such as the electrocardiogram sensing circuit 295. The electrocardiogram can be used by another circuit such as the tachyarrhythmia detection circuit 220 to determine if a tachyarrhythmia is present, such as by comparing a heart rate to a threshold, by examining a morphology of a depolarization, or the like. A non-electrical detector could also be used, such as to mechanically detect heart contractions. At 310, when the implantable medical device senses a tachyarrhythmia, a non-stimulatory electrical energy is then delivered to the heart during the detected tachyarrhythmia, either immediately, after a specified delay, or even recurrently. An electrical energy delivery circuit such as electrical energy delivery circuit 230 can be used to deliver the non-stimulatory electrical energy. At 315, an indication of local myocardial impedance is determined by measuring a response to the non-stimulatory electrical energy. An impedance detection circuit such as impedance detection circuit 240 may be used to measure an indication of the impedance.

Figure 4:
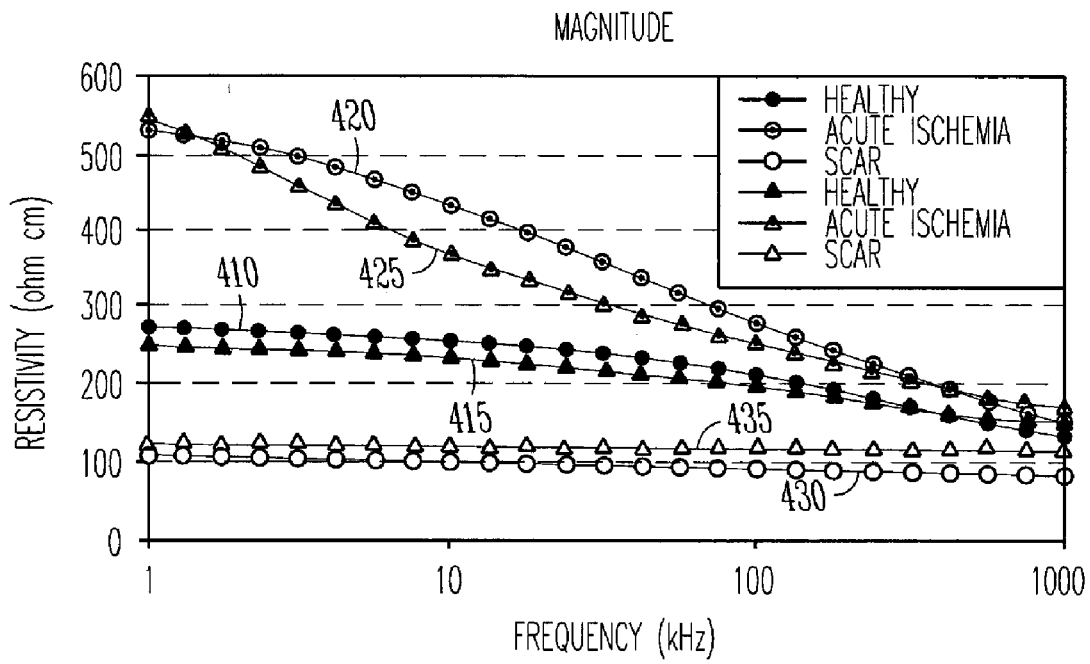
FIG. 4 illustrates an example graph of myocardial impedance of healthy, ischemic, and infarcted hearts as a function of the frequency of a non-stimulation pulse to the heart.

At 320, it is determined whether there is sufficient perfusion to the myocardium during the detected tachyarrhythmia. This perfusion determination can be made by the perfusion measurement circuit 250, which can use the measured indication of myocardial impedance to determine an indication of the perfusion. In general, the local myocardial impedance will vary depending on whether the myocardium is well-perfused, ischemic, or infarcted heart. FIG. 4 illustrates a plot of the local myocardial impedance of a myocardium for a range of frequencies of a non-stimulating pulse. Plots 410 and 415 in FIG. 4 show, for frequencies between 1 and 1,000 kHz, that a healthy well-perfused myocardium exhibits a local myocardial resistivity ranging from slightly less than 200 ohms·cm to slightly less than 300 ohms·cm. Plots 420 and 425 in FIG. 4 illustrate that an ischemic myocardium typically exhibits larger local myocardial resistivities than a healthy well-perfused myocardium, particularly at the lower frequencies. Plots 430 and 435 illustrate that an infarct-scarred myocardium exhibits lower local myocardial resistivities than does a healthy well-perused myocardium. Therefore, a patient having a healthy well-perfused myocardium who experiences an increase in local myocardial impedance, such as during a tachyarrhythmia, may be deemed perfusion-comprised. A patient having a healthy well-perfused myocardium who experiences a decrease in local myocardial impedance may be deemed to have an indication of myocardial infarction.

Figure 5:
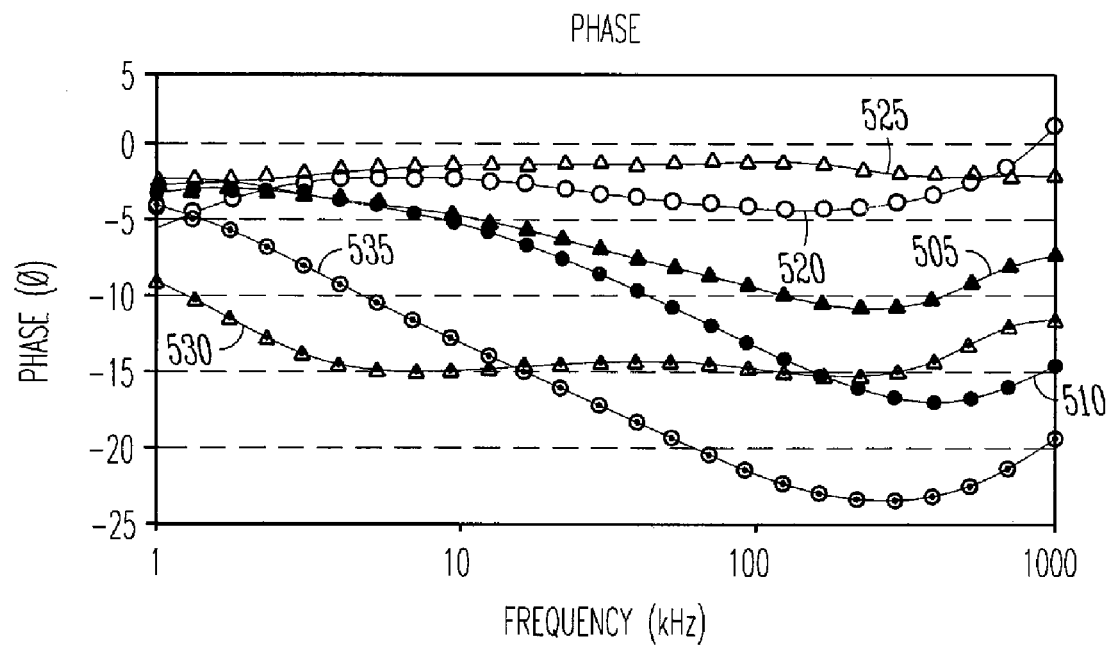
FIG. 5 illustrates an example graph of a phase shift of healthy, ischemic, and infarcted hearts as a function of the frequency of a non-stimulation pulse to the heart.

In an example, the perfusion measurement circuit 250 and the phase detection circuit 245 can determine the perfusion to the heart. FIG. 5 illustrates a plot of a phase angle on the ordinate axis and a frequency of a non-stimulating pulse on the abscissa axis. Plots 505 and 510 illustrate the phase response for a healthy well-perfused heart, plots 520 and 525 illustrate the phase response for an ischemic heart, and plots 530 and 535 illustrate the phase response for an infarcted heart. The perfusion to the heart can be determined by the difference in the phase response as illustrated in FIG. 5, which for the example of FIG. 5, is pronounced in a frequency range of approximately 5 to 30 kHz.

At 320, a decision can be made based upon the perfusion to the heart, such as indicated by the measured local myocardial impedance magnitude or its phase. At 330, if there is sufficient perfusion to the heart, a less aggressive therapy, such as Anti-Tachyarrhythmia Pacing (ATP), can be delivered to the heart in response to the detected tachyarrhythmia. At 335, if there is insufficient perfusion to the heart, a more aggressive therapy, such as a shock, can be delivered in response to the detected tachyarrhythmia.

Figure 6:
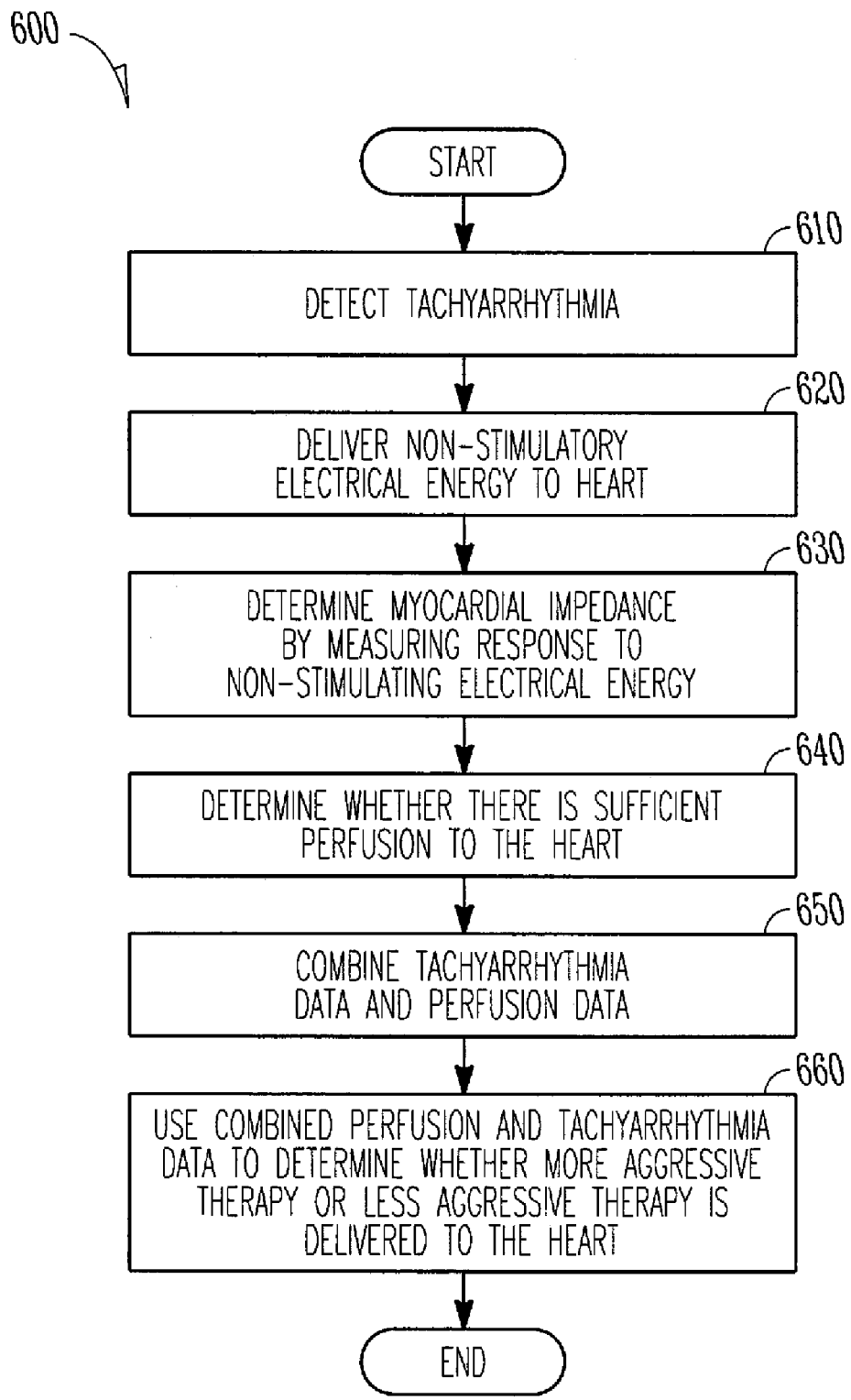
FIG. 6 illustrates an example process to provide electrical stimulation therapy to a patient as a function of perfusion to the patient's heart.

FIG. 6 illustrates an example process 600 to determine the hemodynamic stability of a patient using an implantable medical device such as the implantable medical device 110 of FIG. 2. At 610, a tachyarrhythmia of a heart is detected using an implantable medical device, such as described above. At 620, the implantable medical device delivers non-stimulatory electrical energy to the heart during the detected tachyarrhythmia. At 630, an indication of a local myocardial impedance is determined by measuring a response to the non-stimulatory electrical energy. At 640, it is determined whether there is sufficient perfusion to the heart, such as by using the indication of a local myocardial impedance. At 650, data relating to the tachyarrhythmia, such as rate or morphology data, and data relating to the perfusion of the heart, such as impedance data, are combined, and at 660, the combined data is used to determine whether a less aggressive therapy or a more aggressive therapy is delivered to the heart. In an example, the combination of the tachyarrhythmia electromyocardiogram (EGM) and perfusion data is in the form of a plot of the data in a multi-dimensional feature space, and a statistical technique such as clustering is applied to the plot to determine a decision plane, or hyperplane, or discrete classification zones in a feature space that optimally separate the cases that require less aggressive therapy and those requiring more aggressive therapy. For example, a plot of tachyarrhythmia rate data versus perfusion impedance data may result in substantially two clusters of data on the plot. One cluster of data can indicate a hemodynamically tolerable situation which does not require immediate therapy (or alternatively a less aggressive therapy), and the other cluster of data can indicate a hemodynamically intolerable situation which requires immediate shock therapy. A decision boundary could then be plotted between the two clusters. EGM data and perfusion data from future episodes can then be applied to such a plot, and a determination can be made as to whether the patient is hemodynamically tolerable or intolerable based on what side of the decision boundary the episodic data falls.

Figure 7:
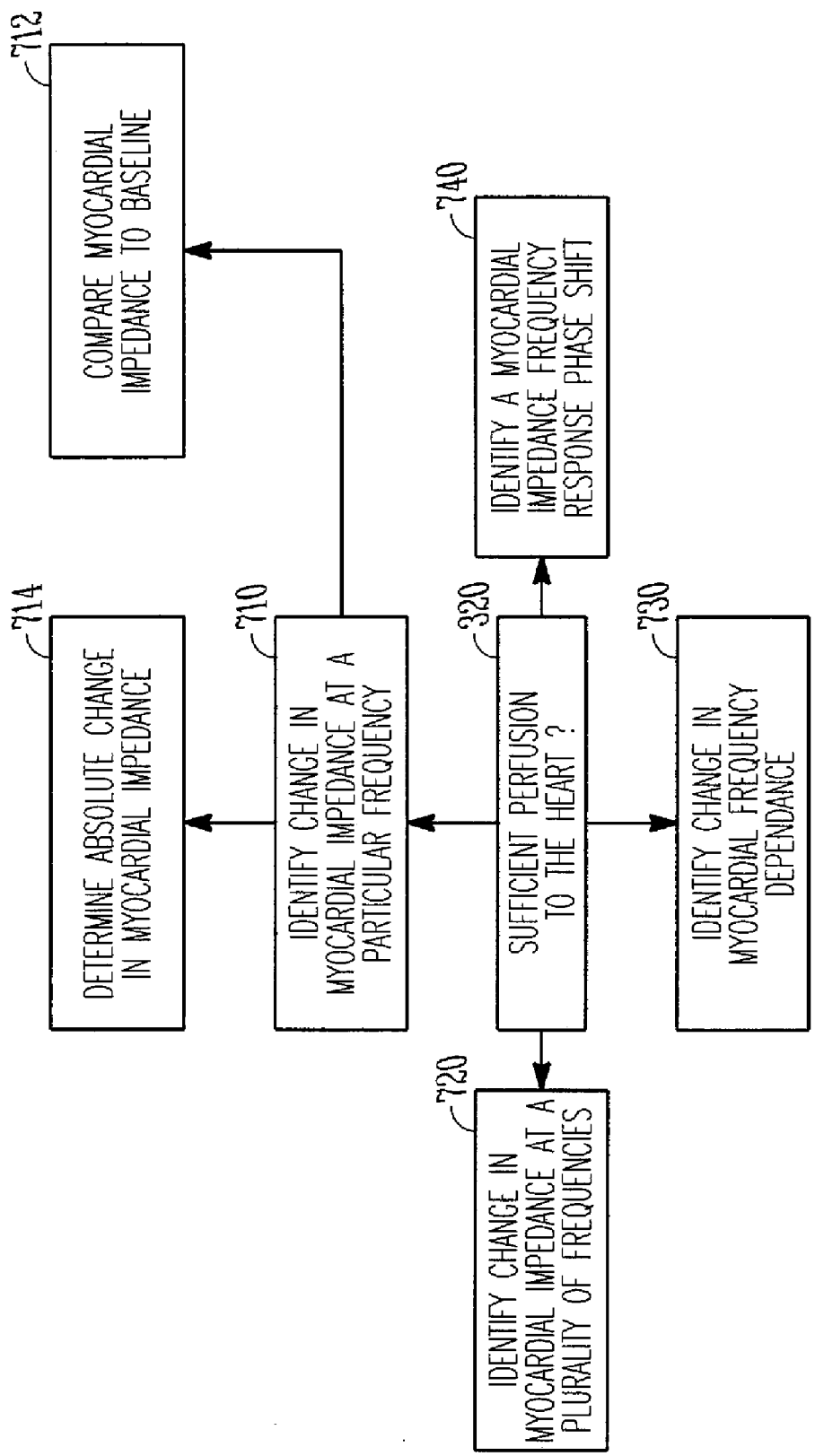
FIG. 7 illustrates several manners in which it can be determined whether a heart is sufficiently perfused.

FIG. 7 illustrates several examples of how the process 300 at 320 can determine whether there is sufficient perfusion to the heart. At 710, perfusion sufficiency is determined by identifying a change in an indication of local myocardial impedance magnitude at a particular frequency of the non-stimulatory electrical energy. At 712, this includes a determination by comparing the myocardial impedance magnitude to a baseline myocardial impedance value. The baseline can be determined for an individual patient based on tests performed on that individual patient, or the baseline can be determined from a population of individuals. Other baseline determination methods can also be used. For example, if it is determined that a sufficiently perfused heart exhibits a baseline myocardial resistivity of approximately 250-300 ohm·cm, then a heart that exhibits a greater myocardial resistivity of for example 500 ohm·cm can be deemed to be an insufficiently perfused heart. At 714, an absolute change in the myocardial impedance magnitude is used to determine perfusion status. For example, if the myocardial resistivity magnitude becomes greater than 500 ohm·cm, then the heart can be deemed insufficiently perfused. An example of the particular frequency of the non-stimulatory electrical energy used to determine the relative or absolute change in myocardial resistivity magnitude includes a frequency value that is in an inclusive range of approximately 5-30 kHz. In another example, the beat to beat change in impedance can be measured. A high degree of variability in the beat to beat impedance indicates normal emptying and filling of the heart chambers. Conversely, small beat to beat changes in impedance indicate poor perfusion and ischemia.

At 720, determining whether there is sufficient perfusion to the heart includes identifying an increase in myocardial impedance frequency response magnitude over a plurality of frequencies at which the non-stimulatory electrical energy is delivered to the heart. For example, FIG. 4 illustrates a myocardial resistivity frequency response magnitude between a healthy heart and an ischemic heart of approximately 300 ohm·cm at a frequency of 1 kHz, and a myocardial resistivity frequency response magnitude of approximately 50 ohm·cm at a frequency of approximately 100 kHz. Consequently, in this example, an insufficiently perfused heart can be identified by these changes at 1 kHZ and 100 kHZ. An example of the plurality of frequencies used to generate the frequency response includes delivering the non-stimulatory energy at different frequencies within an inclusive range of between 1 kHz and 100 kHz.

At 730, determining whether there is sufficient perfusion to the heart includes identifying a change in myocardial impedance frequency dependence over a plurality of frequencies at which the non-stimulatory electrical energy is delivered to the heart. For example, in FIG. 4, the frequency dependence for a healthy heart is differentiable from the frequency dependence of an ischemic heart as exhibited by the difference in slopes of the plots 410 and 415 for a healthy heart and plots 420 and 425 for an ischemic heart. In general, an increase in the absolute value of the negative slope indicates that a heart is becoming or has become ischemic. Thereafter, if the heart becomes infarcted, the absolute value of the slope will decrease again. Since the absolute value of the slope may decrease back to the value at which it was when it was healthy, the myocardial resistivity values must be examined to determine if the heart has indeed become infarcted. An example of the plurality of frequencies of the non-stimulatory energy that is delivered to the heart and that is used to determine the change in myocardial impedance frequency dependence includes a plurality of frequencies within an inclusive range of between 1 kHz and 100 kHz.

At 740, determining whether there is sufficient perfusion to the heart includes identifying a myocardial impedance frequency response phase shift over a plurality of frequencies at which the non-stimulatory electrical energy is delivered to the heart. The myocardial impedance frequency response phase shift can also be determined over a single frequency. As pointed out above, FIG. 5 illustrates several phase responses for a healthy well-perfused heart (505, 510) and an ischemic heart (520, 525). In general, an increase in the absolute value of the phase shift at a particular frequency or over a range of frequencies indicates that a heart is ischemic or is becoming ischemic. An example of the plurality of frequencies of the non-stimulatory energy that is delivered to the heart and that is used to determine the change in myocardial frequency response phase includes a plurality of different frequencies within an inclusive range of between 5 kHz and 30 kHz.

In an example, the non-stimulatory electrical energy delivered to the heart includes delivering to the heart a current defining a current vector. A response to this current vector can be measured. The response can be a voltage as defined by a voltage vector. In certain examples, the current vector and voltage vector are configured in an orthogonal arrangement. This orthogonal arrangement both maximizes the impedance measurement and increases the response sensitivity. In particular, it maximizes the myocardial contribution to the impedance measurement as compared to the contribution by other physiological elements within the thorax. Other current and voltage vector arrangements can also maximize the myocardial contribution to the impedance measurement and increase the response sensitivity such as a bipolar arrangement.

The table below lists several electrode arrangements for current and voltage vectors.

| Current Vector | Voltage Vector |
|---|---|
| RA RING, LV DIST | LV PROX, CAN |
| RA TIP, LV DIST | LV PROX, CAN |
| RA RING, LV PROX | LV DIST, CAN |
| RA TIP, LV PROX | LV DIST, CAN |
| CAN, LV DIST | LV PROX, RA RING |
| CAN, LV DIST | LV PROX, RA TIP |
| CAN, LV PROX | LV DIST, RA RING |
| CAN, LV PROX | LV DIST, RA TIP |
| LV DIST, RA RING | RA TIP, CAN |
| LV PROX, RA RING | RA TIP, CAN |
| LV DIST, RA TIP | RA RING, CAN |
| LV PROX, RA TIP | RA RING, CAN |
| CAN, RA TIP | RA RING, LV DIST |
| CAN, RA TIP | RA RING, LV PROX |
| CAN, RA RING | RA TIP, LV DIST |
| CAN, RA RING | RA TIP, LV PROX |

Figure 8:
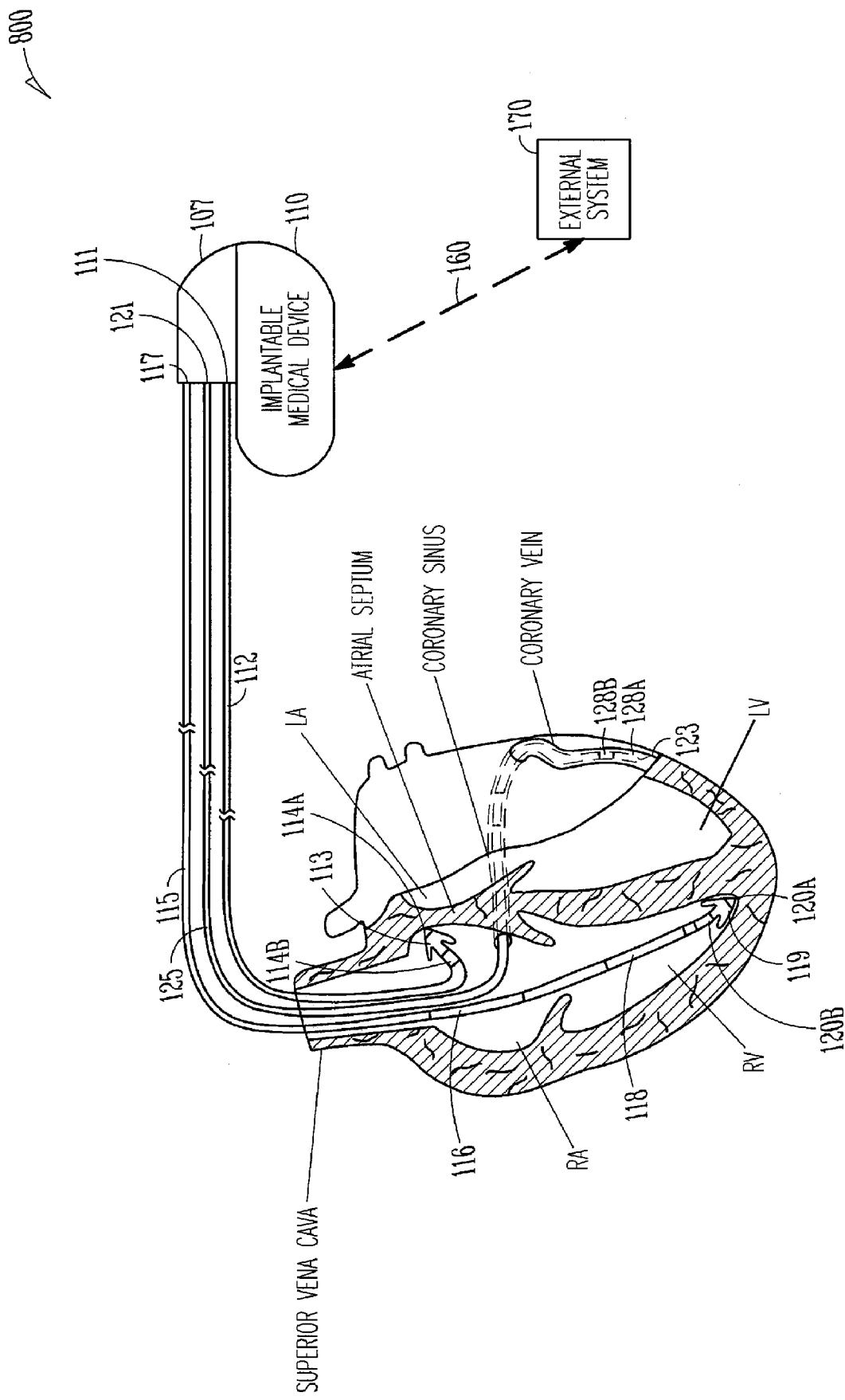
FIG. 8 illustrates an example of an implantable medical device and its associated leads coupled to a heart.

FIG. 8 is an illustration of portions of a system 800 that uses an implantable medical device (IMD) 110. Examples of IMD 110 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 800 shown is used to treat a cardiac arrhythmia. The IMD 110 typically includes an electronics unit coupled by one or more cardiac leads 112, 115, 125, to a heart of a patient or subject. The electronics unit of the IMD 110 typically includes components that are enclosed in a hermetically-sealed canister or "can." The system 800 also typically includes an IMD programmer or other external system 170 that communicates one or more wireless signals 160 with the IMD 110, such as by using radio frequency (RF) or one or more other telemetry signals.

The example shown includes right atrial (RA) lead 112 having an end 111 that is coupled to a header connector 107 and a distal end 113. The distal end 113 is configured for placement in the RA in or near the atrial septum. The RA lead 112 may include a pair of bipolar electrodes, such as an RA tip electrode 114A and an RA ring electrode 114B. The RA electrodes 114A and 114B are incorporated into the lead body at distal end 113 for placement in or near the atrial septum, and are each electrically coupled to IMD 110 through a conductor extending within the lead body. The RA lead is shown placed in or near the atrial septum, but the RA lead may be placed in the atrial appendage or elsewhere.

The example shown also includes a right ventricular (RV) lead 115 having an end 117 that is coupled to the header connector 117 and a distal end 119. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 110, such as through one or more conductors extending within the lead body. The proximal defibrillation electrode 116, distal defibrillation electrode 118, or an electrode formed on the can of IMD 110 allow for delivery of cardioversion or defibrillation pulses to the heart.

The RV tip electrode 120A, RV ring electrode 120B, or an electrode formed on the can of IMD 110 allow for sensing an RV electrogram indicative of RV depolarizations and delivering RV pacing pulses. RA tip electrode 114A, RA ring electrode 114B, or an electrode formed on the can of IMD 110 allow for sensing an RA electrogram indicative of RA depolarizations and allow for delivering RA pacing pulses. Sensing and pacing allows the IMD 110 to adjust timing of the heart chamber contractions. In some examples, the IMD 110 can adjust the timing of ventricular contractions with respect to the timing of atrial contractions by sensing a contraction in the RA and pacing the RV at the desired atrial-ventricular (AV) delay time.

A left ventricular (LV) lead 125 can include a coronary pacing or sensing lead that includes an elongate lead body having an end 121 that is coupled to the header connector 107 and a distal end 123. The distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 110 such as through one or more conductors extending within the lead body. LV tip electrode 128A, LV ring electrode 128B, or an electrode formed on the can of the IMD 110 allow for sensing an LV electrogram indicative of LV depolarizations and delivering LV pacing pulses.

Figure 9:
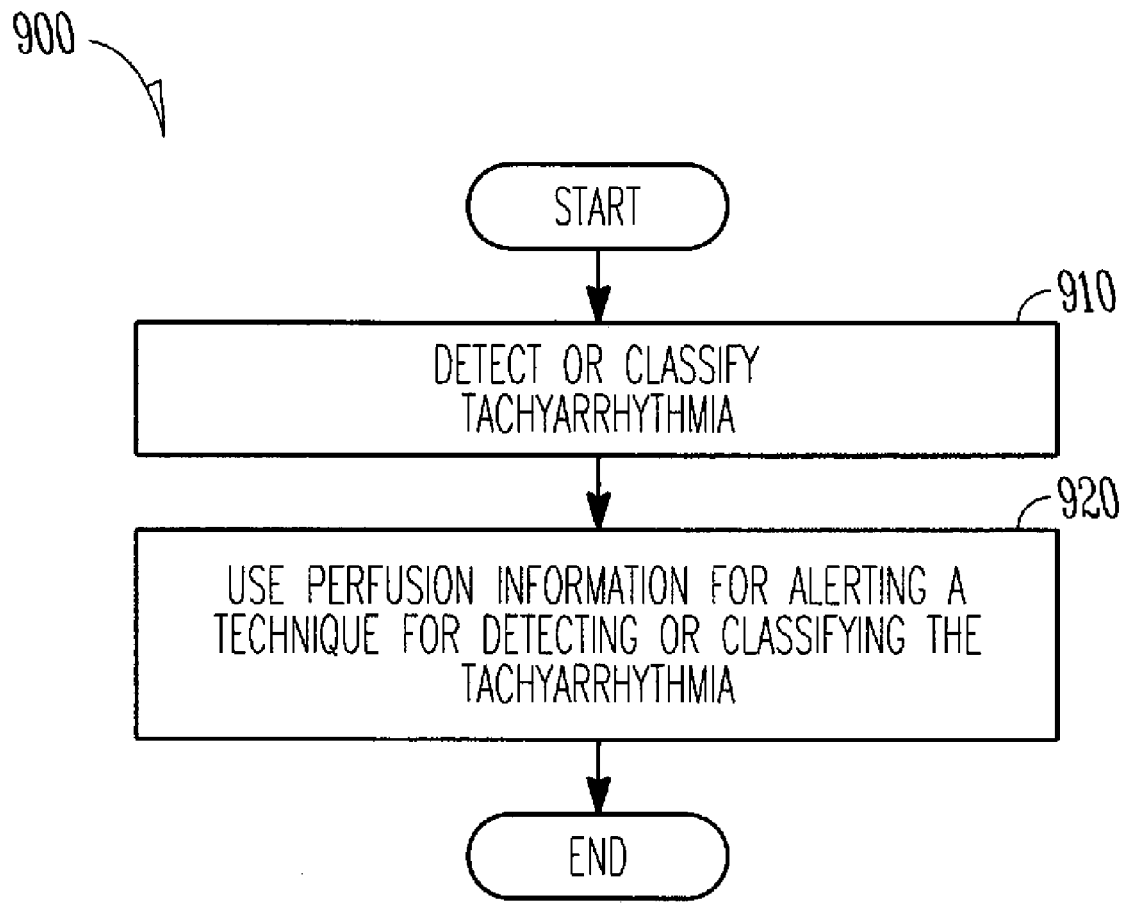
FIG. 9 illustrates an example process to alter thresholds for arrhythmia detection and classification as a function of the perfusion to the heart.

Other forms of electrodes include meshes and patches, which may be applied to one or more portions of heart, or which may be implanted in one or more other areas of the body to help "steer" electrical current produced by the IMD 110 in FIG. 9. The IMDs may be configured with a variety of electrode arrangements or combinations, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of one or more electrical signals related to cardiac activity can provide early, if not immediate, diagnosis of cardiac disease.

FIG. 9 illustrates an example process 900 for detecting or classifying a tachyarrhythmia. At 910, a tachyarrhythmia is detected or classified, such as by using a morphological matching of a cardiac signal with a cardiac signal template, using a rate comparison, or any other tachyarrhythmia detection or classification technique. At 920, perfusion information is used to automatically alter the technique for detecting or classifying the tachyarrhythmia. In an example, tachyarrhythmia detection duration can be altered as a function of the degree of perfusion. The tachyarrhythmia detection duration is the time period that a tachyarrhythmia must persist before it can be declared a true tachyarrhythmia event. For example, if a heart is sufficiently perfused, a longer duration to detect tachyarrhythmia can be tolerated. Similarly, if a heart is insufficiently perfused, a shorter duration to detect tachyarrhythmia can be implemented. In another example, a threshold (e.g., percentage) of correlated heart beats that is used for tachyarrhythmia classification can be automatically altered as a function of perfusion, or a threshold to which a morphological feature correlation coefficient is compared can be automatically altered as a function of the perfusion.

The above description is intended to be illustrative, and not restrictive. For example, the above-described embodiments (or one or more aspects thereof) can be used in combination with each other. Other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

The invention claimed is:

1. A process of using an implantable medical device, the process comprising:
   detecting a tachyarrhythmia of a heart using electrocardiogram (EGM) data obtained with the implantable medical device;
   delivering a non-stimulatory electrical energy to a left ventricle of the heart during the detected tachyarrhythmia using an endovascular lead configured for coupling to the implantable medical device;
   determining a myocardial impedance by measuring a response to the non-stimulatory electrical energy at a myocardial tissue site using the endovascular lead, wherein the delivering the non-stimulatory electrical energy includes delivering a current defining a current vector, and wherein measuring a response to the delivered non-stimulatory electrical energy includes measuring a response voltage defining a voltage vector substantially orthogonal to the current vector;
   determining, during the detected tachyarrhythmia and using the myocardial impedance, information about perfusion to the heart;
   delivering a less aggressive device therapy type in response to the detected tachyarrhythmia when the myocardial impedance indicates that there is sufficient perfusion to the heart; and
   delivering a more aggressive device therapy type in response to the detected tachyarrhythmia when the myocardial impedance indicates that there is insufficient perfusion to the heart.

2. The process of claim 1, wherein the less aggressive therapy comprises Anti-Tachyarrhythmia Pacing (ATP) and the more aggressive therapy comprises a shock.

3. The process of claim 1, wherein determining whether there is sufficient perfusion to the heart comprises identifying a change in myocardial impedance at a particular frequency of the non-stimulatory electrical energy.

4. The process of claim 3, wherein the identifying a change in myocardial impedance includes comparing the myocardial impedance to a baseline myocardial impedance or comparing the myocardial impedance to an absolute threshold.

5. The process of claim 3, wherein the particular frequency of the non-stimulatory electrical energy comprises a frequency value that is in an inclusive range of approximately 5-30 kHz.

6. The process of claim 1, wherein determining whether there is sufficient perfusion to the heart comprises identifying an increase in myocardial impedance frequency response magnitude over a plurality of frequencies at which the non-stimulatory electrical energy is delivered to the heart.

7. The process of claim 6, wherein the plurality of frequencies comprises different frequencies within an inclusive range of between 1 kHz and 100 kHz.

8. The process of claim 1, wherein determining whether there is sufficient perfusion to the heart comprises identifying a change in myocardial impedance magnitude frequency dependence over a plurality of frequencies at which the non-stimulatory electrical energy is delivered to the heart.

9. The process of claim 8, wherein the plurality of frequencies comprises different frequencies within an inclusive range of between 1 kHz and 100 kHz.

10. The process of claim 1, wherein determining whether there is sufficient perfusion to the heart comprises identifying a change in myocardial impedance frequency response phase over a plurality of frequencies at which the non-stimulatory electrical energy is delivered to the heart.

11. The process of claim 10, wherein the plurality of frequencies comprises different frequencies within an inclusive range of between 5 kHz and 30 kHz.

12. The process of claim 1, including:
   combining the EGM data relating to the detected tachyarrhythmia and impedance data relating to the perfusion into a multi-dimensional feature space including a first dimension representing an EGM-derived indication of tachyarrhythmia and a second dimension representing an impedance-derived indication of perfusion; and calculating a decision boundary in the multi-dimensional feature space and using the decision boundary to identify and discriminate between tachyarrhythmia with sufficient perfusion and tachyarrhythmia with insufficient perfusion.

13. The process of claim 12, wherein the combined data comprises a plot of electrocardiogram data versus impedance data, and further comprising calculating an optimal decision hyperplane or a discrete classification zone in the multi-dimensional feature space.

14. The process of claim 1, comprising altering a tachyarrhythmia detection algorithm or a tachyarrhythmia classification technique as a function of the perfusion to the heart.

15. An implantable medical device comprising:
a control circuit;
a tachyarrhythmia detection circuit, coupled to the control circuit, the tachyarrhythmia detection circuit configured to detect a tachyarrhythmia of a heart using electrocardiogram (EGM) data;
an electrical energy delivery circuit, coupled to the control circuit, the electrical delivery circuit configured to deliver non-stimulatory electrical energy to a heart during a detected tachyarrhythmia;
an impedance detection circuit, coupled to the control circuit, the impedance detection circuit configured to detect, when coupled to an endovascular lead, a myocardial impedance by measuring a response to the non-stimulatory electrical energy at a myocardial tissue site using the endovascular lead, wherein the endovascular lead includes a first electrode configured to deliver the non-stimulatory electrical energy to a left ventricle and includes a second electrode to sense the response to the non-stimulatory electrical energy, and wherein the response to the non-stimulatory electrical energy is sensed in a direction orthogonal to a direction of delivery of the non-stimulatory electrical energy;
a perfusion measurement circuit, coupled to the control circuit, the perfusion measurement circuit configured to determine, during a detected tachyarrhythmia and using the myocardial impedance, whether there is sufficient perfusion to the heart; and
a therapy delivery circuit, the therapy delivery circuit configured to deliver a less aggressive therapy type in response to the detected tachyarrhythmia when the myocardial impedance indicates that there is sufficient perfusion to the heart and to deliver a more aggressive therapy type in response to the detected tachyarrhythmia when the myocardial impedance indicates that there is insufficient perfusion to the heart.

16. The implantable medical device of claim 15, wherein the therapy delivery circuit is configured to deliver Anti-Tachyarrhythmia Pacing (ATP) as the less aggressive therapy and shock as the more aggressive therapy.

17. The implantable medical device of claim 15, wherein the perfusion measurement circuit is configured to determine whether there is sufficient perfusion to the heart by identifying a change in myocardial impedance magnitude at a particular frequency of the non-stimulatory electrical energy.

18. The implantable medical device of claim 17, wherein the perfusion measurement circuit is configured to identify the change in myocardial impedance magnitude by comparing the myocardial impedance magnitude to a baseline myocardial impedance magnitude or comparing the myocardial impedance magnitude to an absolute threshold value.

19. The implantable medical device of claim 17, wherein the electrical energy delivery circuit is configured to deliver the particular frequency of the non-stimulatory electrical energy in an inclusive range of approximately 5-30 kHz.

20. The implantable medical device of claim 15, wherein the perfusion measurement circuit is configured to determine whether there is sufficient perfusion to the heart by identifying an increase in myocardial impedance frequency response magnitude over a plurality of frequencies at which the non-stimulatory electrical energy is delivered to the heart.

21. The implantable medical device of claim 20, wherein the electrical energy delivery circuit delivers the plurality of frequencies within an inclusive range of between 1 kHz and 100 kHz.

22. The implantable medical device of claim 15, wherein the perfusion measurement circuit is configured to determine whether there is sufficient perfusion to the heart by identifying a change in myocardial impedance frequency dependence over a plurality of frequencies at which the non-stimulatory electrical energy is delivered to the heart.

23. The implantable medical device of claim 22, wherein the electrical energy deliver circuit delivers the plurality of frequencies within an inclusive range of between 1 kHz and 100 kHz.

24. The implantable medical device of claim 15, wherein the perfusion measurement circuit is configured to determine whether there is sufficient perfusion to the heart by identifying a change in myocardial impedance frequency response phase over a plurality of frequencies at which the non-stimulatory electrical energy is delivered to the heart.

25. The implantable medical device of claim 24, wherein the electrical energy delivery circuit delivers the plurality of frequencies within an inclusive range of between 5 kHz and 30 kHz.

26. The implantable medical device of claim 15, wherein the electrical delivery circuit is configured to deliver the non-stimulatory electrical energy by delivering a current defining a current vector, and wherein measuring a response to the delivered non-stimulatory electrical energy includes measuring a response voltage defining a voltage vector substantially orthogonal to the current vector.

27. The implantable medical device of claim 15, wherein the tachyarrhythmia detection circuit is configured to use the perfusion to the heart for altering a technique for the detecting or classifying the tachyarrhythmia.

28. The implantable medical device of claim 15,
wherein the tachyarrhythmia detection circuit is configured to combine the EGM data relating to the detected tachyarrhythmia and impedance data relating to the perfusion into a multi-dimensional feature space including a first dimension representing an EGM-derived indication of tachyarrhythmia and a second dimension representing an impedance-derived indication of perfusion, and
wherein the perfusion measurement circuit is configured to calculate a decision boundary in the multi-dimensional feature space and to use the decision boundary to identify and discriminate between tachyarrhythmia with sufficient perfusion and tachyarrhythmia with insufficient perfusion.

29. An implantable medical device comprising:

means for detecting a tachyarrhythmia of a heart using electrocardiogram (EGM) data obtained by the implantable medical device;

means for delivering a non-stimulatory electrical energy to a left ventricle of the heart during the detected tachyarrhythmia using an endovascular lead configured to be coupled to the implantable medical device including delivering a current defining a current vector;

means for determining a myocardial impedance by measuring a response to the non-stimulatory electrical energy at a myocardial tissue site of the left ventricle using the endovascular lead including measuring a response voltage defining a voltage vector substantially orthogonal to the current vector;

means for determining, during the detected tachyarrhythmia and using the myocardial impedance, information about perfusion to the heart;

means for delivering a less aggressive device therapy type in response to the detected tachyarrhythmia when the myocardial impedance indicates that there is sufficient perfusion to the heart; and means for delivering a more aggressive device therapy type in response to the detected tachyarrhythmia when the myocardial impedance indicates that there is insufficient perfusion to the heart.

30. The implantable medical device of claim 29, including:

means for combining the EGM data relating to the detected tachyarrhythmia and impedance data relating to the perfusion into a multi-dimensional feature space including a first dimension representing an EGM-derived indication of tachyarrhythmia and a second dimension representing an impedance-derived indication of perfusion; and means for calculating a decision boundary in the multi-dimensional feature space and for using the decision boundary to identify tachyarrhythmia with sufficient perfusion and to identify tachyarrhythmia with insufficient perfusion.

* * * * *